US008795695B2

(12) United States Patent
Smith, III et al.

(10) Patent No.: US 8,795,695 B2
(45) Date of Patent: Aug. 5, 2014

(54) PERSONAL CARE METHODS

(75) Inventors: Edward Dewey Smith, III, Mason, OH (US); Jason Edward Cook, Anderson Township, OH (US); Shawn David McConaughy, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/585,865

(22) Filed: Aug. 15, 2012

(65) Prior Publication Data
US 2013/0045255 A1 Feb. 21, 2013

Related U.S. Application Data

(60) Provisional application No. 61/523,816, filed on Aug. 15, 2011, provisional application No. 61/523,824, filed on Aug. 15, 2011.

(51) Int. Cl.
*A61K 8/02* (2006.01)

(52) U.S. Cl.
USPC ........................................................ 424/401

(58) Field of Classification Search
None
See application file for complete search history.

(56) References Cited

U.S. PATENT DOCUMENTS

| | | | |
|---|---|---|---|
| 2,438,091 A | 3/1948 | Lynch et al. |
| 2,528,378 A | 10/1950 | Mannheimer et al. |
| 2,658,072 A | 11/1953 | Kosmin et al. |
| 2,809,971 A | 10/1957 | Bernstein et al. |
| 3,235,455 A | 2/1966 | Judge et al. |
| 3,281,366 A | 10/1966 | Judge et al. |
| 3,412,033 A | 11/1968 | Karsten et al. |
| 3,689,437 A | 9/1972 | McLaughlin |
| 3,725,547 A | 4/1973 | Kooistra |
| 3,761,418 A | 9/1973 | Parran, Jr. |
| 3,949,137 A | 4/1976 | Akrongold |
| 4,181,632 A | 1/1980 | Schebece |
| 4,190,550 A | 2/1980 | Campbell |
| 4,207,198 A | 6/1980 | Kenkare |
| 4,328,131 A | 5/1982 | Carson, Jr. et al. |
| 4,335,025 A | 6/1982 | Barker et al. |
| 4,345,080 A | 8/1982 | Bolich, Jr. |
| 4,367,999 A | 1/1983 | Benuzzi |
| 4,379,753 A | 4/1983 | Bolich, Jr. |
| 4,396,766 A | 8/1983 | Farmer, Jr. et al. |
| 4,510,641 A | 4/1985 | Morris |
| 4,515,703 A | 5/1985 | Haq |
| 4,554,097 A | 11/1985 | Schebece et al. |
| 4,565,693 A | 1/1986 | Marschner |
| 4,603,069 A | 7/1986 | Haq et al. |
| 4,654,158 A | 3/1987 | Shepherd |
| 4,665,580 A | 5/1987 | Morris |
| 4,670,430 A | 6/1987 | Imamura et al. |
| 4,708,863 A | 11/1987 | Bews et al. |
| 4,714,563 A | 12/1987 | Kajs et al. |
| 4,735,739 A | 4/1988 | Floyd et al. |
| 4,812,253 A | 3/1989 | Small et al. |
| 4,861,508 A | 8/1989 | Wegener et al. |
| 4,935,158 A | 6/1990 | Aszman et al. |
| 4,953,250 A | 9/1990 | Brown |
| 4,987,632 A | 1/1991 | Rowe et al. |
| 5,011,681 A | 4/1991 | Ciotti et al. |
| 5,037,818 A | 8/1991 | Sime |
| 5,066,494 A | 11/1991 | Becher |
| 5,104,645 A | 4/1992 | Cardin et al. |
| 5,104,646 A | 4/1992 | Bolich, Jr. et al. |
| 5,106,609 A | 4/1992 | Bolich, Jr. et al. |
| 5,108,642 A | 4/1992 | Aszman et al. |
| 5,132,115 A | 7/1992 | Wolter et al. |
| 5,139,705 A | 8/1992 | Wittpenn, Jr. et al. |
| 5,225,097 A | 7/1993 | Kacher et al. |
| 5,227,086 A | 7/1993 | Kacher et al. |
| 5,262,079 A | 11/1993 | Kacher et al. |
| 5,264,144 A | 11/1993 | Moroney et al. |
| 5,264,145 A | 11/1993 | French et al. |
| 5,308,180 A | 5/1994 | Pournoor et al. |
| 5,312,559 A | 5/1994 | Kacher et al. |
| RE34,692 E | 8/1994 | Becher |
| 5,340,492 A | 8/1994 | Kacher et al. |
| 5,387,362 A | 2/1995 | Tollens et al. |
| 5,393,466 A | 2/1995 | Ilardi et al. |
| 5,433,883 A | 7/1995 | Massaro et al. |
| 5,433,894 A | 7/1995 | Massaro et al. |
| 5,482,643 A | 1/1996 | Chambers et al. |
| 5,487,884 A | 1/1996 | Bissett et al. |
| 5,520,840 A | 5/1996 | Massaro et al. |
| 5,523,017 A | 6/1996 | Moran et al. |
| 5,536,492 A | 7/1996 | Mitchnick et al. |
| 5,540,854 A | 7/1996 | Fair et al. |
| 5,540,860 A | 7/1996 | Hosseini et al. |
| 5,573,699 A | 11/1996 | Jones et al. |

(Continued)

FOREIGN PATENT DOCUMENTS

| | | |
|---|---|---|
| CA | 2012123 A1 | 9/1990 |
| CA | 2012124 A1 | 9/1990 |

(Continued)

OTHER PUBLICATIONS

U.S. Appl. No. 13/856,457, filed Apr. 4, 2013, Edward Dewey Smith, III et al.
U.S. Appl. No. 13/890,369, filed May 9, 2013, Edward Dewey Smith, III et al.
Photographs of DermaZinc Zinc Therapy Bar by Dermalogix Partners, Inc. purchased from DERMAdoctor.com via Amazon Marketplace on May 23, 2011 and believed to have been on the market in the US at least a year before the filed of this application.
Photographs of ZNP Bar by Stiefel Laboratories, Inc. believed to have been on the market in the US at least a year before the filed of this application.
PCT International Search Report and Written Opinion for PCT/US2012/032054 dated Jul. 4, 2012.

(Continued)

*Primary Examiner* — Bethany Barham
*Assistant Examiner* — Olga V Tcherkasskaya

(57) ABSTRACT

Methods are provided to enhance deposition of zinc pyrithione.

18 Claims, No Drawings

(56) References Cited

U.S. PATENT DOCUMENTS

| | | | |
|---|---|---|---|
| 5,612,301 A | 3/1997 | Inman | |
| 5,652,228 A | 7/1997 | Bissett | |
| 5,681,852 A | 10/1997 | Bissett | |
| 5,683,971 A | 11/1997 | Rose et al. | |
| 5,683,973 A | 11/1997 | Post et al. | |
| 5,696,083 A * | 12/1997 | Nelson, Jr. | 514/2.9 |
| 5,698,475 A | 12/1997 | Vlasblom | |
| 5,702,992 A | 12/1997 | Martin et al. | |
| 5,703,025 A | 12/1997 | Zyngier et al. | |
| 5,704,723 A | 1/1998 | Salisian | |
| 5,756,438 A | 5/1998 | Rau et al. | |
| 5,786,311 A | 7/1998 | Zyngier et al. | |
| 5,824,296 A | 10/1998 | Dubief et al. | |
| 5,886,031 A | 3/1999 | Shin et al. | |
| 5,888,953 A | 3/1999 | Harris et al. | |
| 5,916,856 A | 6/1999 | Massaro et al. | |
| 5,968,852 A | 10/1999 | Vlasblom | |
| 5,972,860 A | 10/1999 | Eshita et al. | |
| 5,985,808 A | 11/1999 | He et al. | |
| 6,015,547 A | 1/2000 | Yam | |
| 6,017,562 A | 1/2000 | Kaufman et al. | |
| 6,017,936 A | 1/2000 | Polson et al. | |
| 6,026,534 A | 2/2000 | Gonda et al. | |
| 6,028,042 A | 2/2000 | Chambers et al. | |
| 6,063,390 A | 5/2000 | Farrell et al. | |
| 6,071,543 A | 6/2000 | Thornfeldt | |
| 6,074,997 A | 6/2000 | Rau et al. | |
| 6,096,297 A | 8/2000 | Jones et al. | |
| 6,132,743 A | 10/2000 | Kuroda et al. | |
| 6,153,208 A | 11/2000 | McAtee et al. | |
| 6,162,446 A | 12/2000 | Hani et al. | |
| 6,162,457 A | 12/2000 | Martz | |
| 6,206,863 B1 | 3/2001 | Skewes et al. | |
| 6,217,854 B1 | 4/2001 | Farrell et al. | |
| 6,242,007 B1 | 6/2001 | Mohseni et al. | |
| 6,245,343 B1 | 6/2001 | Roulier et al. | |
| 6,277,360 B1 | 8/2001 | Carew et al. | |
| 6,322,801 B1 | 11/2001 | Lorenzi et al. | |
| 6,328,811 B1 | 12/2001 | Martin et al. | |
| 6,335,002 B1 | 1/2002 | Kogoi et al. | |
| 6,376,046 B1 | 4/2002 | Hoshino et al. | |
| 6,383,999 B1 * | 5/2002 | Coyle et al. | 510/146 |
| 6,391,835 B1 | 5/2002 | Gott et al. | |
| 6,395,691 B1 | 5/2002 | Tsaur | |
| 6,428,799 B1 | 8/2002 | Cen et al. | |
| 6,432,432 B1 | 8/2002 | Mohseni et al. | |
| 6,447,759 B2 | 9/2002 | Noguchi et al. | |
| 6,451,300 B1 | 9/2002 | Dunlop et al. | |
| 6,465,015 B1 | 10/2002 | Mohseni et al. | |
| 6,467,981 B1 | 10/2002 | Gueret | |
| 6,482,839 B1 | 11/2002 | Thornfeldt | |
| 6,488,943 B1 | 12/2002 | Beerse et al. | |
| 6,491,928 B1 | 12/2002 | Smith, III | |
| 6,491,933 B2 | 12/2002 | Lorenzi et al. | |
| 6,491,937 B1 | 12/2002 | Slavtcheff et al. | |
| 6,547,468 B2 | 4/2003 | Gruenbacher et al. | |
| 6,550,092 B1 | 4/2003 | Brown et al. | |
| 6,607,739 B1 | 8/2003 | Wallo | |
| 6,638,527 B2 | 10/2003 | Gott et al. | |
| 6,638,611 B2 | 10/2003 | Seth | |
| 6,645,611 B2 | 11/2003 | Seth | |
| 6,649,155 B1 | 11/2003 | Dunlop et al. | |
| 6,673,755 B2 * | 1/2004 | Wei et al. | 510/130 |
| 6,673,756 B2 * | 1/2004 | Sonnenberg et al. | 510/141 |
| 6,677,294 B2 | 1/2004 | Shaw et al. | |
| 6,682,724 B2 | 1/2004 | Mohseni et al. | |
| 6,730,317 B2 | 5/2004 | Gueret | |
| 6,753,063 B1 | 6/2004 | Pung et al. | |
| 6,783,294 B2 | 8/2004 | Duden et al. | |
| 6,835,701 B2 | 12/2004 | Seipel et al. | |
| 6,867,380 B2 | 3/2005 | Miki et al. | |
| 6,878,380 B2 | 4/2005 | Farrell et al. | |
| 6,883,353 B2 | 4/2005 | Goldoni et al. | |
| 6,887,859 B2 | 5/2005 | Clapp et al. | |
| 6,902,338 B2 | 6/2005 | Puvvada et al. | |
| 6,903,057 B1 | 6/2005 | Tsaur | |
| 6,906,016 B1 | 6/2005 | Tsaur | |
| 6,942,878 B2 | 9/2005 | Ishii et al. | |
| 6,974,569 B2 | 12/2005 | Dunlop et al. | |
| 6,977,238 B1 | 12/2005 | Wetzel et al. | |
| 6,992,054 B2 | 1/2006 | Lee et al. | |
| 7,026,308 B1 | 4/2006 | Gavin et al. | |
| 7,033,064 B2 | 4/2006 | Ida | |
| 7,033,964 B2 | 4/2006 | Gillette | |
| 7,101,612 B2 | 9/2006 | Lang et al. | |
| 7,115,535 B1 | 10/2006 | Smith, III et al. | |
| 7,115,551 B2 | 10/2006 | Hasenoehrl et al. | |
| 7,229,956 B2 | 6/2007 | Bedford et al. | |
| 7,276,459 B1 | 10/2007 | Lang et al. | |
| 7,288,513 B2 | 10/2007 | Taylor et al. | |
| 7,320,953 B2 | 1/2008 | Grissett et al. | |
| 7,335,626 B2 | 2/2008 | Keenan et al. | |
| 7,345,014 B2 | 3/2008 | Keenan et al. | |
| 7,348,029 B2 | 3/2008 | Kliss et al. | |
| 7,348,299 B2 | 3/2008 | Keenan et al. | |
| 7,381,415 B2 | 6/2008 | Yokoyama et al. | |
| 7,381,692 B2 | 6/2008 | Grissett et al. | |
| 7,381,693 B2 | 6/2008 | Keenan et al. | |
| 7,419,321 B2 | 9/2008 | Tereschouk | |
| 7,452,547 B2 | 11/2008 | Lambino et al. | |
| 7,462,348 B2 | 12/2008 | Gruenbacher et al. | |
| 7,514,071 B2 | 4/2009 | Simon et al. | |
| 7,544,367 B2 | 6/2009 | Mohseni et al. | |
| 7,581,273 B2 | 9/2009 | Dobrin et al. | |
| 7,584,519 B2 | 9/2009 | Ouellette et al. | |
| 7,651,290 B2 | 1/2010 | Bauer et al. | |
| 7,659,397 B2 | 2/2010 | Hidaka | |
| 7,674,058 B2 | 3/2010 | Berger Sharp et al. | |
| 7,674,785 B2 | 3/2010 | Gavin et al. | |
| 7,846,462 B2 | 12/2010 | Spadini et al. | |
| 7,874,756 B2 | 1/2011 | Nuebel et al. | |
| 8,147,853 B2 | 4/2012 | Taylor et al. | |
| 8,157,464 B2 | 4/2012 | Prax | |
| 8,158,566 B2 | 4/2012 | Wei | |
| 8,304,070 B2 | 11/2012 | Yabuki et al. | |
| 8,308,388 B2 | 11/2012 | Guay | |
| 8,343,469 B2 | 1/2013 | Bierganns et al. | |
| 8,357,383 B2 | 1/2013 | Spadini et al. | |
| 8,475,817 B2 | 7/2013 | Hasenoehrl et al. | |
| 8,491,877 B2 | 7/2013 | Schwartz et al. | |
| 8,534,947 B2 | 9/2013 | Prax | |
| 2001/0003565 A1 | 6/2001 | Mcosker et al. | |
| 2001/0028894 A1 | 10/2001 | Gueret | |
| 2002/0178507 A1 | 12/2002 | Goldoni et al. | |
| 2002/0192268 A1 | 12/2002 | Alwattari et al. | |
| 2003/0079323 A1 | 5/2003 | Ngai | |
| 2003/0140439 A1 | 7/2003 | Durden et al. | |
| 2003/0143263 A1 | 7/2003 | Durden et al. | |
| 2003/0144160 A1 * | 7/2003 | Wei et al. | 510/130 |
| 2003/0180242 A1 | 9/2003 | Eccard et al. | |
| 2003/0194425 A1 | 10/2003 | Simon et al. | |
| 2003/0203010 A1 | 10/2003 | Wallo | |
| 2003/0224028 A1 | 12/2003 | Galey | |
| 2003/0228352 A1 | 12/2003 | Hasenoehrl et al. | |
| 2004/0116017 A1 | 6/2004 | Smith, III et al. | |
| 2004/0147189 A1 | 7/2004 | Smith, III et al. | |
| 2004/0161435 A1 | 8/2004 | Gupta | |
| 2004/0170670 A1 | 9/2004 | Smith et al. | |
| 2004/0175343 A1 | 9/2004 | Osborne et al. | |
| 2004/0176002 A1 | 9/2004 | Siegwart | |
| 2004/0191331 A1 | 9/2004 | Schwartz et al. | |
| 2004/0213751 A1 | 10/2004 | Schwartz et al. | |
| 2004/0223991 A1 * | 11/2004 | Wei et al. | 424/401 |
| 2004/0237234 A1 | 12/2004 | Young et al. | |
| 2004/0237235 A1 | 12/2004 | Visioli et al. | |
| 2005/0118276 A1 | 6/2005 | Lei et al. | |
| 2005/0148260 A1 | 7/2005 | Kopacz et al. | |
| 2005/0202068 A1 | 9/2005 | Hasenoehrl et al. | |
| 2005/0244352 A1 | 11/2005 | Lemoine et al. | |
| 2005/0271595 A1 | 12/2005 | Brown | |
| 2005/0276827 A1 | 12/2005 | Macedo et al. | |
| 2005/0276828 A1 | 12/2005 | Grissett et al. | |
| 2006/0024381 A1 | 2/2006 | Schwartz et al. | |
| 2006/0078524 A1 * | 4/2006 | Midha et al. | 424/70.12 |

(56) References Cited

U.S. PATENT DOCUMENTS

| | | | |
|---|---|---|---|
| 2006/0079419 A1* | 4/2006 | Wagner et al. | 510/130 |
| 2006/0079420 A1* | 4/2006 | Wagner et al. | 510/130 |
| 2006/0079421 A1* | 4/2006 | Wagner et al. | 510/130 |
| 2006/0079422 A1* | 4/2006 | Midha et al. | 510/130 |
| 2006/0097170 A1 | 5/2006 | Prinz et al. | |
| 2006/0111259 A1 | 5/2006 | Chakrabarty et al. | |
| 2006/0121807 A1* | 6/2006 | Albrecht et al. | 442/121 |
| 2006/0141014 A1 | 6/2006 | Eknoian et al. | |
| 2006/0171971 A1* | 8/2006 | Marsh et al. | 424/401 |
| 2006/0246119 A1 | 11/2006 | Eknoian et al. | |
| 2007/0009463 A1 | 1/2007 | Niebauer et al. | |
| 2007/0009472 A1 | 1/2007 | Niebauer et al. | |
| 2007/0048359 A1 | 3/2007 | Bolton | |
| 2007/0071797 A1 | 3/2007 | Hernandez-Munoa et al. | |
| 2007/0099813 A1 | 5/2007 | Luizzi et al. | |
| 2007/0107151 A1* | 5/2007 | Pung et al. | 15/104.94 |
| 2007/0128147 A1 | 6/2007 | Schwartz et al. | |
| 2007/0130706 A1 | 6/2007 | Buhrow et al. | |
| 2007/0130707 A1 | 6/2007 | Cohen et al. | |
| 2007/0190177 A1 | 8/2007 | Kling et al. | |
| 2007/0280976 A1* | 12/2007 | Taylor et al. | 424/401 |
| 2007/0283516 A1 | 12/2007 | Rasmussen et al. | |
| 2008/0104787 A1 | 5/2008 | Keenan et al. | |
| 2008/0116096 A1 | 5/2008 | Johnson et al. | |
| 2008/0138441 A1 | 6/2008 | Schwartz et al. | |
| 2008/0138442 A1 | 6/2008 | Johnson et al. | |
| 2008/0145388 A1 | 6/2008 | Roreger et al. | |
| 2008/0160093 A1 | 7/2008 | Schwartz et al. | |
| 2008/0168748 A1 | 7/2008 | McCloskey | |
| 2008/0247806 A1 | 10/2008 | Todd et al. | |
| 2008/0249136 A1 | 10/2008 | Annis et al. | |
| 2008/0299269 A1 | 12/2008 | Mane et al. | |
| 2009/0028808 A1 | 1/2009 | Cetti et al. | |
| 2009/0178692 A1 | 7/2009 | Warr et al. | |
| 2009/0246376 A1 | 10/2009 | Gunn et al. | |
| 2009/0324520 A1 | 12/2009 | Cetti et al. | |
| 2010/0104871 A1 | 4/2010 | Hashimoto et al. | |
| 2010/0130988 A1 | 5/2010 | Bolton | |
| 2010/0272829 A1 | 10/2010 | Hidaka | |
| 2010/0322878 A1 | 12/2010 | Stella et al. | |
| 2010/0330008 A1 | 12/2010 | Izu et al. | |
| 2011/0002970 A1 | 1/2011 | Parashar | |
| 2011/0009302 A1* | 1/2011 | Soffin et al. | 510/127 |
| 2011/0132387 A1* | 6/2011 | Alwattari et al. | 132/200 |
| 2011/0152433 A1 | 6/2011 | Bechtloff et al. | |
| 2011/0195098 A1* | 8/2011 | Glenn et al. | 424/401 |
| 2011/0197906 A1 | 8/2011 | Schwartz | |
| 2011/0197907 A1 | 8/2011 | Schwartz | |
| 2011/0200649 A1 | 8/2011 | Schwartz et al. | |
| 2011/0200650 A1 | 8/2011 | Schwartz | |
| 2011/0201588 A1 | 8/2011 | Schwartz | |
| 2011/0278429 A1 | 11/2011 | Jha et al. | |
| 2011/0290904 A1 | 12/2011 | Mane et al. | |
| 2012/0009285 A1 | 1/2012 | Wei et al. | |
| 2012/0028869 A1 | 2/2012 | Crawford et al. | |
| 2012/0039966 A1 | 2/2012 | Capretta et al. | |
| 2012/0076747 A1 | 3/2012 | Bierganns et al. | |
| 2012/0103151 A1 | 5/2012 | Jones et al. | |
| 2012/0128777 A1 | 5/2012 | Keck et al. | |
| 2012/0141737 A1 | 6/2012 | Yabuki et al. | |
| 2012/0216408 A1 | 8/2012 | Cook et al. | |
| 2012/0219610 A1 | 8/2012 | Smith et al. | |
| 2012/0220516 A1 | 8/2012 | Smith, III et al. | |
| 2012/0246851 A1 | 10/2012 | Smith, III et al. | |
| 2012/0246852 A1 | 10/2012 | Smith, III et al. | |
| 2012/0252715 A1 | 10/2012 | McConaughy et al. | |
| 2012/0263661 A1 | 10/2012 | Grune | |
| 2012/0324736 A1 | 12/2012 | Eagleton | |
| 2013/0042482 A1 | 2/2013 | Bradford et al. | |
| 2013/0043145 A1 | 2/2013 | Smith, III et al. | |
| 2013/0043146 A1 | 2/2013 | Smith, III et al. | |
| 2013/0043147 A1 | 2/2013 | Smith, III et al. | |
| 2013/0045248 A1 | 2/2013 | Coffindaffer et al. | |
| 2013/0045255 A1 | 2/2013 | Smith, III et al. | |
| 2013/0045256 A1 | 2/2013 | Schwartz | |
| 2013/0045257 A1 | 2/2013 | Alwattari et al. | |
| 2013/0045263 A1 | 2/2013 | Smith, III et al. | |
| 2013/0045284 A1 | 2/2013 | Stella | |
| 2013/0045285 A1 | 2/2013 | Stella et al. | |
| 2013/0045907 A1 | 2/2013 | Lanzalaco et al. | |
| 2013/0045961 A1 | 2/2013 | Smith, III et al. | |
| 2013/0048005 A1 | 2/2013 | Smith, III et al. | |
| 2013/0118518 A1 | 5/2013 | Spadini et al. | |
| 2013/0205959 A1 | 8/2013 | Jones et al. | |
| 2013/0266622 A1 | 10/2013 | Mcconnaughy et al. | |
| 2013/0280200 A1 | 10/2013 | Schwartz | |

FOREIGN PATENT DOCUMENTS

| | | |
|---|---|---|
| CN | 1046273 | 10/1990 |
| CN | 1117835 | 3/1996 |
| CN | 1318622 | 10/2001 |
| CN | 1433966 A | 8/2003 |
| CN | 101024737 A | 8/2007 |
| CN | 101543466 A | 9/2009 |
| CN | 101711887 A | 5/2010 |
| CN | 101817548 A | 9/2010 |
| DE | 19744213 | 4/1999 |
| DE | 20017205 | 12/2000 |
| DE | 10208678 A1 | 9/2002 |
| DE | 20304298 | 6/2003 |
| DE | 10301838 | 7/2004 |
| DE | 102004007851 | 8/2004 |
| EP | 0 034 385 B1 | 8/1981 |
| EP | 0 093 541 A2 | 11/1983 |
| EP | 0032793 B1 | 3/1984 |
| EP | 0047116 B1 | 7/1985 |
| EP | 0 158 481 A2 | 10/1985 |
| EP | 0161911 | 11/1985 |
| EP | 0 196 824 A2 | 10/1986 |
| EP | 0211664 | 2/1987 |
| EP | 0 217 635 A2 | 4/1987 |
| EP | 0272492 A2 | 6/1988 |
| EP | 0 285 388 A2 | 10/1988 |
| EP | 0353013 | 1/1990 |
| EP | 387693 | 9/1990 |
| EP | 387694 | 9/1990 |
| EP | 0 468 564 A2 | 1/1992 |
| EP | 0863201 A2 | 9/1998 |
| EP | 1000605 A2 | 5/2000 |
| EP | 1106165 | 6/2001 |
| EP | 1153554 A1 | 11/2001 |
| EP | 1140033 B | 10/2005 |
| EP | 2105061 | 9/2009 |
| EP | 1143897 B2 * | 12/2009 |
| FR | 1190521 | 10/1959 |
| FR | 2822045 | 9/2002 |
| FR | 2855741 | 12/2004 |
| FR | 2867067 A1 | 9/2005 |
| GB | 2 130 965 A | 6/1984 |
| GB | 2163947 A | 3/1986 |
| GB | 2222526 A | 3/1990 |
| GB | 2 303 541 A | 2/1997 |
| JP | 61277608 A2 | 12/1986 |
| JP | 02265516 | 10/1990 |
| JP | 08084684 | 4/1996 |
| JP | 09299271 | 11/1997 |
| JP | 10000170 | 1/1998 |
| JP | 10183194 A1 | 7/1998 |
| JP | 11302144 A | 11/1999 |
| JP | 2002142857 | 5/2002 |
| JP | 2002275031 | 9/2002 |
| JP | 2002315689 | 10/2002 |
| JP | 2004016560 | 1/2004 |
| JP | 2004236996 | 8/2004 |
| JP | 2006082263 | 3/2006 |
| JP | 2006130194 | 5/2006 |
| JP | 2006176675 A | 6/2006 |
| JP | 2008094917 A | 4/2008 |
| JP | 2009292750 | 12/2009 |
| JP | 2010046129 | 3/2010 |
| JP | 2010120863 A | 6/2010 |
| JP | 2011111454 A | 6/2011 |
| SE | 8703015 | 2/1989 |

(56) References Cited

FOREIGN PATENT DOCUMENTS

| WO | 94/14408 A1 | 7/1994 |
|---|---|---|
| WO | 94/14409 A1 | 7/1994 |
| WO | 95/00116 | 1/1995 |
| WO | 95/11887 | 5/1995 |
| WO | 95/26710 A1 | 10/1995 |
| WO | 96/631187 A2 | 3/1996 |
| WO | 97/04683 | 2/1997 |
| WO | 98/27193 A1 | 6/1998 |
| WO | 2009/828399 A1 | 7/1998 |
| WO | 99/25318 A1 | 5/1999 |
| WO | 99/31184 | 6/1999 |
| WO | 99/66886 A1 | 12/1999 |
| WO | 00/35413 A1 | 6/2000 |
| WO | 01/08655 A1 | 2/2001 |
| WO | 01/08658 A1 | 2/2001 |
| WO | 02/00178 A1 | 1/2002 |
| WO | 02/092050 A2 | 11/2002 |
| WO | 03/053397 A1 | 3/2003 |
| WO | WO2004031449 A2 | 4/2004 |
| WO | 2006/036976 | 4/2006 |
| WO | 2006/110386 A1 | 10/2006 |
| WO | 2008/113973 A1 | 9/2008 |
| WO | WO2010018418 A1 | 2/2010 |
| WO | WO2010073815 A1 | 7/2010 |

OTHER PUBLICATIONS

PCT International Search Report and Written Opinion for PCT/US2012/032111 dated Dec. 17, 2012.
International Search Report and Written Opinion of PCT/US00/01387 dated Sep. 20, 2000.
International Search Report and Written Opinion of PCT/US2012/050873 dated Dec. 10, 2012.
International Search Report and Written Opinion of PCT/US2012/050874 dated Dec. 12, 2012.
International Search Report and Written Opinion of PCT/US2012/050877 dated Dec. 6, 2012.
Arch Zinc Pyrithione Product Stewardship Summary, Aug. 2008.
Photographs of Johnson's Super Sudzer e-z grip soap purchased from Kroger stores around Aug. 2010 and believed to have been on the market in the US at least two years before the filed of this application.
Photographs of Jonson's Buddies, easy-grip sudzing bar purchased from Target stores around Aug. 2010 and believed to have been on the market in the US at least two years before the filed of this application.

* cited by examiner

PERSONAL CARE METHODS

CROSS REFERENCE TO RELATED CASES

This application claims the benefit of U.S. Provisional Application No. 61/523,816, filed Aug. 15, 2011 and U.S. Provisional Application No. 61/523,824, filed Aug. 15, 2011 which are incorporated herein by reference.

TECHNICAL FIELD

The present disclosure generally relates to methods of enhancing deposition of zinc pyrithione.

BACKGROUND

Human health is impacted by many microbial entities or microbials such as germs, bacteria, fungi, yeasts, molds, viruses, or the like. For example, invasion by microbial entities including various viruses and bacteria cause a wide variety of sicknesses and ailments. To reduce such an invasion, people frequently wash their skin with antimicrobial soaps. Antimicrobial soaps typically include soaps in combination with, for example, antimicrobial agents. For example, one such antibacterial soap is a bar soap with zinc pyrithione. When the skin is washed with an antimicrobial soap, the surfactancy of the soap typically removes most of the microbial entities on the skin, while the antimicrobial agent, such as zinc pyrithione, deposits onto the skin to provide residual protection against subsequent invasion.

However, current antibacterial soap regimens can be improved if such soaps were to deposit more of the antimicrobial agent or if the antimicrobial agent was more bioavailable. By improving bioavailability and/or deposition of zinc pyrithione, enough zinc pyrithione particulates can be present to prevent subsequent invasion by gram negative bacteria such as *E. coli*, gram positive bacteria, and the like. Accordingly, it would be desirable to provide a personal care compositions and methods for improving the antimicrobial efficacy and bioavailability of zinc pyrithione.

SUMMARY

A method of enhancing deposition of zinc pyrithione to skin, comprising: applying a cleansing composition to at least a portion of the skin of an individual and then applying a composition comprising zinc pyrithione to the same portion of skin of the individual.

A method of enhancing deposition of zinc pyrithione to skin, comprising: formulating a personal care composition comprising zinc pyrithione with about 15% or less, by weight of the composition, of wax.

DETAILED DESCRIPTION

I. Definitions

As used herein, the following terms shall have the meaning specified thereafter:

"Anhydrous" refers to those compositions, and components thereof, which are substantially free of water.

"Bar soap" refers to compositions intended for topical application to a surface such as skin or hair to remove, for example, dirt, oil, and the like. The bar soaps can be rinse-off formulations, in which the product is applied topically to the skin or hair and then subsequently rinsed within minutes from the skin or hair with water. The product could also be wiped off using a substrate. Bar soaps can be in the form of a solid (e.g., non-flowing) bar soap intended for topical application to skin. The bar soap can also be in the form of a soft solid which is compliant to the body. The bar soap additionally can be wrapped in a substrate which remains on the bar during use.

"Cleansing composition" refers to compositions intended for topical application to a surface such as skin and/or hair to remove, for example, dirt, oil, and the like. The cleansing compositions disclosed herein can be rinse-off formulations, in which the product is applied topically to the skin or hair via, for example, an implement or substrate and then subsequently rinsed within seconds to minutes from the skin and/or hair with water.

"Conform/Conformable" as used herein refers to an article and/or composition that has a conformance value of 5 or more in at least one direction as measured according to the Cantilever Compliance test set out below.

"Compliant" as used herein refers to an article and/or composition with a compliance value of about 1.5 kg/mm or less as measured according to the Compliance Test set out below.

"Dried zinc pyrithione" refers to zinc pyrithione that has about 25% or less, by weight of the zinc pyrithione, of moisture.

"Natural" refers to materials that can be derived from plants, animals, insects, or materials that can be byproducts of plants, animals, or insects.

"Non-compliant" refers to an article or composition with a compliance value of 2.0 kg/mm or more as measured according to the Compliance Test set out below.

"Personal care" refers to a composition or article for topical application to skin and/or hair. Personal care compositions can be rinse-off formulations, in which the composition can be applied topically to the skin and/or hair and then subsequently rinsed within seconds to minutes of application. The composition could also be wiped off using a substrate.

"Structured" refers to having a rheology that can confer stability on the personal care composition. A cleansing phase can be considered to be structured if the cleansing phase has one or more following characteristics: (a) Zero Shear Viscosity of at least 100 Pascal-seconds (Pa-s), at least about 200 Pa-s, at least about 500 Pa-s, at least about 1,000 Pa-s, at least about 1,500 Pa-s, or at least about 2,000 Pa-s; (b) A Structured Domain Volume Ratio as measured by the Ultracentrifugation Method described hereinafter, of about 40% or more, about 45% or more, about 50% or more, about 55% or more, about 60% or more, about 65% or more, about 70% or more, about 75% or more, about 80% or more, about 85% or more, or about 90% or more; or (c) A Young's Modulus of about 2 Pascals (Pa) or more, about 10 Pa or more, about 20 Pa or more, about 30 Pa or more, about 40 Pa or more, about 50 Pa or more, about 75 Pa or more, or about 100 Pa or more.

"Substantially free of" refers to about 5% or less, about 3% or less, about 1% or less, or about 0.1% or less of a stated ingredient. "Free of" refers to no detectable amount of the stated ingredient or thing.

"Substrate" refers to a material which can limit the amount of water to which a personal care composition is exposed during a usage event versus exposure of a personal care composition itself absent a substrate. The substrate may be, for example, a film, formed film, batting, woven, nonwoven, or a combination thereof.

"Synthetic" refers to materials that can be obtained primarily from various man-made materials or from natural materials which have been altered.

"Usage event" refers to one 5 minute cycle of the Consumption Test below.

"Water penetrable substrate" refers to a substrate which provides sufficient water to penetrate the personal care article to provide desired lather capabilities.

II. Methods of Enhancing Deposition of Zinc Pyrithione

Many current antimicrobial soaps work by depositing an antimicrobial agent on the skin. The length of the effect of the antimicrobial soap, however, depends on both the amount of antimicrobial agent deposited and on the efficiency of the antimicrobial agent deposited. It has surprisingly been found that application of zinc pyrithione (ZPT) after cleansing results in more of the antimicrobial being deposited on the skin than simultaneously cleansing and applying.

For example, the Deposition Table below shows the results of deposition tests performed on various formulations with care articles allowing for sequential cleansing then deposition. The difference in the products is that the deposition composition of F has 15% wax, while the deposition composition of G has 20% wax. The product with the lower amount of wax, F, deposited more ZPT (0.98 μg/cm$^2$) than G with the higher wax content (0.64 μg/cm$^2$). This same phenomenon was also observed in products with simultaneous cleanse and deposit. See, for example, products I and J where the difference in wax between the two simultaneous delivery products is that product I contains only 15% while product I contains 20%. Product J had a significantly higher ZPT deposition of 0.83 μg/cm$^2$ versus the deposition of 0.01 μg/cm$^2$ seen in product J.

| Composition & Form | ZPT Material | Deposition onto pigskin (μg/cm$^2$) |
|---|---|---|
| bar soap with ZPT (simultaneous) (A) | 0.2% FPS | 0.0 (below detection) |
| bar soap with ZPT (simultaneous) (B) | 0.2% Tray-dried ZPT powder | 0.05 |
| Personal Care Article w/personal care composition of 60/40 soap/glycerin paste containing 2% ZPT (simultaneous) (C) | 2% FPS | 0.06 |
| 2-zoned Personal Care Article (sequential clean then deposit) (D) Cleansing step 1: 60/40 soap/glycerin paste zone 1 Depo step 2: 0.5% ZPT in aq. laponite gel zone 2 | 0.5% FPS | 1.05 |
| Personal Care Article (simultaneous clean & deposit; Control for previous) (E) ZPT in aq. laponite gel blended into 60/40 paste | 0.5% FPS | 0.02 |
| 2-zone Personal Care Article (sequential clean then deposit) (F) Cleansing step 1: 60/40 soap/glycerin paste side 1 Depo step 2: soybean oil/15% wax with tray dried ZPT | 0.5% Tray-dried ZPT powder | 0.98 |
| 2-zone Personal Care Article (sequential clean then deposit) (G) Cleansing step 1: 60/40 soap/glycerin paste side 1 Depo step 2: soybean oil/20% wax with tray dried ZPT | 0.5% Tray-dried ZPT powder | 0.64 |
| 2-zone Personal Care Article (sequential clean then deposit) (H) Cleansing step 1: 60/40 soap/glycerin paste side 1 Depo step 2: soybean oil/20% wax with tray dried ZPT [substrate variation: CPM only, no microapertured layer | 0.5% Tray-dried ZPT powder | 1.11 |
| 3-zone Personal Care Article (simultaneous clean & deposit but Cleaning from one location and depo from second location in Article) (I) Cleansing zones (2 ends): 60/40 soap/glycerin paste Depo zone: soybean oil/15% wax with tray dried ZPT | 0.5% Tray-dried ZPT powder | 0.83 |
| 3-zone Personal Care Article (simultaneous clean & deposit but Cleaning from one location and depo from second location in Article) (J) Cleansing zones (2 ends): 60/40 soap/glycerin paste Depo zone: soybean oil/20% wax with tray dried ZPT | 0.5% Tray-dried ZPT powder | 0.01 | the Cup Scrub Procedure. As shown below, pig skins were tested to monitor and evaluate the deposition of zinc pyrithione using personal cleansing compositions and articles. The multi-zoned personal care articles which allowed for sequential, versus simultaneous, delivery illustrate increased deposition over other embodiments tested.

See for example, the results for compositions H and J. Products H and J have the same cleansing and deposition compositions in their zones, but H allows for sequential cleanse and deposit while J only gives simultaneous cleanse and deposit. As can be seen below, H has a significantly higher deposition of ZPT (1.11 μg/cm$^2$) than J (0.01 μg/cm$^2$). This is also seen in products D and E. Product D is a 2-zone personal care article allowing sequential cleaning and deposition, while product E is a blended version of the cleansing and deposition compositions in D. Product D has a significantly highly ZPT deposition (1.05 μg/cm$^2$) than E (0.02 μg/cm$^2$).

A second phenomenon observed based on the deposition testing below is the impact of the amount of wax in the deposition composition to deposition of ZPT. See, for example, products F and G. Both of these are 2-zone personal Thus, as can be seen from above, there are multiple avenues to increase the deposition of ZPT. First, one can enhance the deposition of ZPT to the skin of an individual, by applying a cleansing composition to a portion of the skin and then applying a composition comprising zinc pyrithione to the same portion of skin of the individual. The method may further include rinsing the skin after cleansing and before application of the ZPT composition. The method may also further include rinsing after application of the ZPT composition. For the sake of brevity, the more detailed information relating to the compositions may be found below and can be included in the method herein.

Another method to enhance deposition of ZPT to skin includes formulating a personal care composition comprising zinc pyrithione with about 15% or less, by weight of the composition, of wax. The personal care composition comprising zinc pyrithione may have about 13% or less, about 11% or less, about 9% or less, about 5% or less, about 3% or less, by weight of the personal care composition, of wax. The personal care composition may be substantially free of or free of wax. The personal care composition may also be substantially free of or free of surfactant. The personal care composition may comprise a benefit phase. For the sake of brevity, the more detailed information relating to the compositions may be found below and can be included in the method herein.

Zinc Pyrithione

Conventional zinc pyrithione can be made, for example, by reacting 1-hydroxy-2-pyridinethione (i.e., pyrithione acid) or a soluble salt thereof with a zinc salt (e.g. zinc sulfate) to form a zinc pyrithione precipitate as illustrated in U.S. Pat. No. 2,809,971, and the zinc pyrithione can be formed or processed into platelets using, for example, sonic energy as illustrated in U.S. Pat. No. 6,682,724. These processes, however, do not include drying. Conventional zinc pyrithione is often in a slurry form (i.e. particles in water) and one example of a conventional ZPT in slurry form, FPS ZPT, has a moisture content of about 52%.

Dried zinc pyrithione can be formed from one or more of a variety of drying processes. Examples of such drying processes can include, but are not limited to spray drying, tray drying, tunnel drying, roller drying, fluidized bed drying, pneumatic drying, rotary drying, trough drying, bin drying, belt drying, vacuum drying, drum drying, infrared drying, microwave drying, and radiofrequency drying.

A drying process can be utilized to reduce the amount of moisture in zinc pyrithione. Dried zinc pyrithione may have a moisture content of about 25% or less, by weight of the dried zinc pyrithione. The dried zinc pyrithione may have an even lower moisture content, for example by being dried further, and that moisture content could be 22%, 20, 18, 15, 12, 10, 8, 6, 5, 3, or 1%, or less, by weight of the dried zinc pyrithione. While some types of drying are exemplified herein, any appropriate method to reduce moisture level can be used.

Dried zinc pyrithione may be subject to further processing, like milling, depending on the requirements for the particular application. Examples of milling can include, but are not limited to pin milling and jet milling.

Dried zinc pyrithione can further be treated before being used in a personal care composition. For example, zinc pyrithione can be stabilized against flocculation. Thus, dried zinc pyrithione (e.g., particulate and/or platelet form) used in a personal care composition may have a surface modification thereon to prevent the particulates and/or platelets from attaching to each other. The surface modification can include polynaphthalene sulfonate or any other suitable sulfate, sulfonate, carboxylate, or other compound that provides stability, for example, by charge or steric barrier on a surface.

Primary particles of zinc pyrithione can be formed from a precipitation process, and upon being dried, can join together to form larger, aggregate particles. Primary particles of dried zinc pyrithione can be, for example, in the form of particulates, platelets, or a combination thereof. The primary particles can, for example, comprise an average primary particle size from about 0.1 µm to about 5 µm. Dried zinc pyrithione primary particulates can, for example, comprise an average particle size from about 0.3 µm to about 15 µm or from about 0.5 µm to about 10 µm. Aggregate particulates can comprise an aggregate mean particle size from about 0.3 microns to about 25 microns. One means of determining aggregate particle is with conventional light scattering techniques for powders using e.g., a Malvern Mastersizer.

Primary particles and aggregate particles can be bound during a drying process by atomic or molecular forces. Zinc pyrithione can be dried with excipients, for example, materials that enhance bioactivity. Examples of suitable bioactivity enhancing excipients include metallic carbonates, auxiliary active such as selenium compounds, organic actives such as triclosan or trichlorocarbanilide, acidic or basic actives, combinations thereof, and the like. Additionally, properties of aggregate particles can be manipulated in order to change bioavailability. For example, aggregate particles can be formed so as to contain no internal porosity or aggregate particles can be formed with void spaces to have a high internal porosity such that the aggregate particles can maintain properties relating to surface area.

Without wishing to be bound by theory, it is believed that a personal care composition including dried zinc pyrithione can provide zinc pyrithione having a primary particle size, an aggregate particle size, and a frangibility to increase efficacy and deposition. In particular, it is believed that an aggregate particle can more readily engage a surface of the skin of an individual, and as the aggregate particle breaks apart into primary particles, the dried zinc pyrithione can be more readily deposited on the skin, thus enhancing deposition of the zinc pyrithione. The aggregate particles can be durable to survive processing into the personal care composition. However, the aggregate particles can also be frangible such that abrasive forces used during application to the skin and/or hair can release the primary particles from the aggregate particles. Further, it is believed that increasing the surface area of the zinc pyrithione increases its bioavailability and this increases its efficacy. This can be done, for example, by making thinner particles or by introducing void spaces into the particles. It is believed the dried ZPT can have an increased surface area due to its structure containing void spaces.

Personal Care Composition

A personal care composition can include zinc pyrithione. The zinc pyrithione may be in any suitable form, for example, slurry or dried powder. The zinc pyrithione may be present from about 0.01% to about 5%, by weight of the personal care composition. It may be present at even smaller amounts like from about 0.05% to about 2%, from about 0.1% to about 2%, or at about 0.5%, by weight of the personal care composition, for example.

Many personal care compositions can be water-based. As such, a personal care composition can include from about 0.1% to about 35%, from about 0.3% to about 20%, or about 10%, by weight of the personal care composition, of water. It should be understood that an amount of water can be lost, i.e. evaporated, during a process of making a personal care composition, or subsequently, with water being absorbed by surrounding packaging (e.g. a cardboard carton), and the like. Thus, a personal care composition can also include materials that tend to bind the water such that the water can be maintained in the personal care composition at the desired levels. Examples of such materials can include carbohydrate structurants and humectants such as glycerin. However, it will be appreciated that a personal care composition can be anhydrous.

A variety of optional ingredients can also be added to a personal care composition. Such suitable ingredients can include, but are not limited to, structurants, humectants, fatty acids, inorganic salts, and other antimicrobial agents or actives.

A personal care composition can also optionally include hydrophilic structurants such as carbohydrate structurants and gums. Some suitable carbohydrate structurants include raw starch (corn, rice, potato, wheat, and the like) and pregelatinized starch. Some suitable gums include carrageenan and xanthan gum. A personal care composition may include from about 0.1% to about 30%, from about 2% to about 25%, or from about 4% to about 20%, by weight of the personal care composition, of a carbohydrate structurant.

A personal care composition can also optionally include one or more humectants. Examples of such humectants can include polyhydric alcohols. Further, humectants such as glycerin can be included the personal care composition as a result of production or as an additional ingredient. For example, glycerin can be a by-product after saponification of the personal care composition. Including additional humectant can result in a number of benefits such as improvement in hardness of the personal care composition, decreased water activity of the personal care composition, and reduction of a weight loss rate of the personal care composition over time due to water evaporation.

A personal care composition can optionally include inorganic salts. Inorganic salts can help to maintain a particular water content or level of the personal care composition and improve hardness of the personal care composition. The inorganic salts can also help to bind the water in the personal care composition to prevent water loss by evaporation or other means. A personal care composition can optionally include from about 0.01% to about 15%, from about 1% to about 12%, or from about 2.5% to about 10.5%, by weight of the personal care composition, of inorganic salt. Examples of suitable inorganic salts can include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and tetrasodium pyrophosphate.

A personal care composition can optionally further include one or more additional antibacterial agents that can serve to further enhance antimicrobial effectiveness of the personal care composition. A personal care composition can include, for example, from about 0.001% to about 2%, from about 0.01% to about 1.5%, or from about 0.1% to about 1%, by weight of the personal care composition, of additional antibacterial agent(s). Examples of suitable antibacterial agents can include carbanilides, triclocarban (also known as trichlorocarbanilide), triclosan, a halogenated diphenylether available as DP-300 from Ciba-Geigy, hexachlorophene, 3,4,5-tribromosalicylanilide, and salts of 2-pyridinethiol-1-oxide, salicylic acid, and other organic acids. Other suitable antibacterial agents are described in U.S. Pat. No. 6,488,943.

Solid Personal Care Compositions

As noted herein, personal care compositions can take on numerous forms. One suitable form is that of a solid personal care composition. Solid compositions can take many forms like powder, pellets, bars, etc. These forms will generally be described herein as bar soap, but it should be understood that the solid composition could be in another form or shape. One example of a bar soap personal care composition can include from about 0.1% to about 35%, by weight of the personal care composition, of water, from about 45% to about 99%, by weight of the personal care composition, of soap, and from about 0.01% to about 5%, by weight of the personal care composition, of dried zinc pyrithione. Another suitable antimicrobial bar soap can include, for example, from about 0.1% to about 30%, by weight of the personal care composition, of water, from about 40% to about 99%, by weight of the personal care composition, of soap, and from about 0.01% to about 1%, by weight of the personal care composition, of dried zinc pyrithione.

Bar soap compositions can be referred to as conventional solid (i.e. non-flowing) bar soap compositions. Some bar soap composition comprise convention soap, while others contain synthetic surfactants, and still others contain a mix of soap and synthetic surfactant. Bar compositions may include, for example, from about 0% to about 45% of a synthetic anionic surfactant. An example of a suitable conventional soap can include milled toilet bars that are unbuilt (i.e. include about 5% or less of a water-soluble surfactancy builder).

A personal care bar composition can include, for example from about 45% to about 99% or from about 50% to about 75%, by weight of the personal care composition, of soap. Such soaps can include a typical soap, i.e., an alkali metal or alkanol ammonium salt of an alkane- or alkene monocarboxylic acid. Sodium, magnesium, potassium, calcium, mono-, di- and tri-ethanol ammonium cations, or combinations thereof, can be suitable for a personal care composition. The soap included in a personal care composition can include sodium soaps or a combination of sodium soaps with from about 1% to about 25% ammonium, potassium, magnesium, calcium, or a mixture of these soaps. Additionally, the soap can be well-known alkali metal salts of alkanoic or alkenoic acids having from about 12 to about 22 carbon atoms or from about 12 to about 18 carbon atoms. Another suitable soap can be alkali metal carboxylates of alkyl or alkene hydrocarbons having from about 12 to about 22 carbon atoms. Additional suitable soap compositions are described in U.S. patent application Ser. No. 13/036,889.

A personal care composition can also include soaps having a fatty acid. For example, one bar soap composition could use from about 40% to about 95% of soluble alkali metal soap of $C_8$-$C_{24}$ or $C_{10}$-$C_{20}$ fatty acids. The fatty acid may, for example, have a distribution of coconut oil that can provide a lower end of a broad molecular weight range or a fatty acid distribution of peanut or rapeseed oil, or their hydrogenated derivatives, which can provide an upper end of the broad molecular weight range. Other such compositions can include a fatty acid distribution of tallow and/or vegetable oil. The tallow can include fatty acid mixtures that can typically have an approximate carbon chain length distribution of 2.5% $C_{14}$, 29% $C_{16}$, 23% $C_{18}$, 2% palmitoleic, 41.5% oleic, and 3% linoleic. The tallow can also include other mixtures with a similar distribution, such as fatty acids derived from various animal tallows and/or lard. In one example, the tallow can also be hardened (i.e., hydrogenated) such that some or all unsaturated fatty acid moieties can be converted to saturated fatty acid moieties.

Suitable examples of vegetable oil include palm oil, coconut oil, palm kernel oil, palm oil stearine, soybean oil, and hydrogenated rice bran oil, or mixtures thereof, since such oils can be among more readily available fats. One example of a suitable coconut oil can include a proportion of fatty acids having at least 12 carbon atoms of about 85%. Such a proportion can be greater when mixtures of coconut oil and fats such as tallow, palm oil, or non-tropical nut oils or fats can be used where principle chain lengths can be $C_{16}$ and higher. The soap included in a personal care composition can be, for example, a sodium soap having a mixture of about 67-68% tallow, about 16-17% coconut oil, about 2% glycerin, and about 14% water.

Soap included in a personal care composition can also be unsaturated in accordance with commercially acceptable standards. For example, a soap included in a personal care composition could include unsaturation in a range of from about 37% to about 45% of saponified material.

Soaps included in a personal care composition can be made, for example, by a classic kettle boiling process or modern continuous soap manufacturing processes wherein natural fats and oils such as tallow or coconut oil or their equivalents can be saponified with an alkali metal hydroxide using procedures well known to those skilled in the art. Soap can also be made by neutralizing fatty acids such as lauric ($C_{12}$), myristic ($C_{14}$), palmitic ($C_{16}$), or stearic ($C_{18}$) acids, with an alkali metal hydroxide or carbonate.

Soap included in a personal care composition could also be made by a continuous soap manufacturing process. The soap could be processed into soap noodles via a vacuum flash drying process. One example of a suitable soap noodle comprises about 67.2% tallow soap, about 16.8% coconut soap, about 2% glycerin, and about 14% water, by weight of the soap noodle. The soap noodles can then be utilized in a milling process to finalize a personal care composition.

A personal care composition can also optionally include one or more free fatty acids at an amount of from about 0.01% to about 10%, from about 0.5% to about 2%, or from about 0.75% to about 1.5%, by weight of the personal care composition. Free fatty acids can be included in the personal care composition to provide enhanced skin feel benefits such as softer and smoother feeling skin. Suitable free fatty acids can include tallow, coconut, palm, and palm kernel fatty acids.

A solid personal care composition can have compliant or non-compliant characteristics. For example, if the personal care composition is a compliant personal cleansing composition for cleansing the skin, then the composition will bend to some degree to more fully contact a curved portion of the body, such as an arm. Thus, if the compliant personal cleansing composition is originally flat with no curve, when applied to an arm for cleansing there would be some amount of bend to better fit to the arm. Likewise, if the composition's shape has a small amount of a curve, when applied to the arm the composition would bend to some degree to more fully contact the arm. Oppositely, if the original personal care composition is curved such that it would not need to bend to fit to a curved surface like the arm, then it would bend to straighten when applied to a less curved surface like an abdomen.

In certain examples, compliance of a personal care composition can be measured according to the Compliance Test described in more detail below. In certain examples, a personal care composition can comprise a compliance value of about 1.50 kg/mm or less. In certain examples, the compliance value of the personal care composition can be about 1.35 kg/mm or less; about 1.25 kg/mm or less; about 1.2 kg/mm or less; about 1.1 kg/mm or less; or about 1.0 kg/mm or less. In certain examples, the personal care composition can have a compliance of about 0.01 kg/mm to about 1.50 kg/mm; about 0.03 kg/mm to about 1.50 kg/mm; about 0.05 kg/mm to about 1.25 kg/mm; about 0.05 kg/mm to about 1.15 kg/mm; and/or about 0.10 kg/mm to about 1.1 kg/mm.

In some examples, the composition can become compliant after exposure to water. Thus, you may have a non-compliant composition that, after exposure to a liquid, like water, during a usage event, becomes compliant. If a composition becomes compliant by the end of a second usage event, then it is considered compliant.

A non-compliant composition has a compliance value of 2.0 kg/mm or more. Non-compliant compositions require more than an average force used during cleansing to follow the line of the surface to which it is applied or will not change shape at all. Non-compliant compositions may further have a compliance value of about 2.5 kg/mm or more.

Solid personal care compositions may further be used to form a personal care article. A personal care article can include a substrate and a personal care composition. The personal care article may also comprise multiple substrates and/or multiple personal care compositions. The compositions may be compliant, non-compliant, or a combination thereof. A personal care article comprising a solid personal care composition may be conformable or non-compliant. A conformable personal care article has a conformance value of about 5 or more in at least one direction as measured on the Cantilever Compliance test set out below. A conformable personal care article may have a conformance value of about 10 or more, about 30 or more, from about 50 to about 90, or any combination thereof, in at least one direction as measured by the Cantilever Compliance test.

Personal care articles and there components are more fully described in U.S. application Ser. No. 13/438,918. The solid personal care compositions may have any of the properties as noted above.

Liquid Personal Care Compositions

Personal care compositions can take on many forms and one of those suitable forms can be a liquid form. Examples of personal care compositions in liquid form can include hand soap, body wash, hand sanitizers, etc. Such liquid-based personal care compositions can include a cleansing phase and/or a benefit phase (i.e., a single- or multi-phase composition). Each of a cleansing phrase or a benefit phase can include various components. The liquid composition can have multiple phases in varying combinations. For example, a personal care composition can include two cleansing phase, a cleansing phase and a benefit phase, two benefit phases, or any acceptable combination of phases. Additionally, the phases in a multi-phase composition can be blended, separate, or a combination thereof. The phases may also form a pattern (e.g. striped). A personal care composition may be micellar, lamellar, or a combination thereof. A personal care composition could comprise at least a 70% lamellar structure. A dried ZPT may be placed in a cleansing phase.

A cleansing phase may be aqueous or anhydrous. A cleansing phase may also, for example, include alcohol. A cleansing phase may comprise a surfactant. Surfactants suitable for use herein include anionic, zwitterionic, amphoteric, and combinations thereof. One example of a suitable surfactant comprises sodium laureth-1 sulfate, such that the dried zinc pyrithione can be used in a micellar body wash, which is described in greater detail below.

A cleansing phase may include an aqueous structured surfactant phase from about 5% to about 20%, by weight of the personal care composition. Such a structured surfactant phase can include, for example, sodium trideceth(n) sulfate, hereinafter STnS, wherein n can define average moles of ethoxylation. n can range from about 0 to about 3, from about 0.5 to about 2.7, from about 1.1 to about 2.5, from about 1.8 to about 2.2, or n can be about 2. When n can be less than 3, STnS can provide improved stability, improved compatibility of benefit agents within personal care compositions, and increased mildness of the personal care compositions, such described benefits of STnS are disclosed in U.S. patent application Ser. No. 13/157,665.

A cleansing phase can also comprise at least one of an amphoteric surfactant and a zwitterionic surfactant. Suitable amphoteric or zwitterionic surfactants can include, for example, those described in U.S. Pat. No. 5,104,646 and U.S. Pat. No. 5,106,609.

A cleansing phase can also comprise a structuring system. One example of a structuring system includes a non-ionic emulsifier, an associative polymer, an electrolyte, or a combination thereof.

A personal care composition can be optionally free of sodium lauryl sulfate, hereinafter SLS. However, when SLS is present, suitable examples of SLS are described in U.S. patent application Ser. No. 12/817,786.

A personal care composition can include from about 0.1% to 20%, by weight of the personal care composition, of a cosurfactant. Cosurfactants can comprise amphoteric surfactants, zwitterionic surfactants, or mixtures thereof. Examples of suitable amphoteric or zwitterionic surfactants can include those described in U.S. Pat. No. 5,104,646 and U.S. Pat. No. 5,106,609.

Amphoteric surfactants can include those that can be broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoactetate, disodium lauroamphoacetate disodium cocodiamphoacetate, and mixtures thereof. Amphoacetates and diamphoacetates can also be used.

Zwitterionic surfactants suitable for use can include those that are broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocoamidopropyl betaine.

Other optional additives can be included in the cleansing phase, including for example emulsifiers (e.g., non-ionic emulsifier) and electrolytes. Suitable emulsifiers and electrolytes are described in U.S. patent application Ser. No. 13/157,665.

Personal care compositions can also include a benefit phase. The benefit phase can be hydrophobic and/or anhydrous. The benefit phase can also be substantially free of or free of surfactant. A benefit phase can also include a benefit agent. In particular, a benefit phase can comprise from about 0.1% to about 50%, by weight of the personal care composition, of a benefit agent or from about 0.5% to about 20%, by weight of the personal care composition, of a benefit agent. Examples of the benefit agent can include petrolatum, glyceryl monooleate, mineral oil, triglycerides, soybean oil, castor oil, soy oligomers, and mixtures thereof. Additional examples of benefit agents can include water insoluble or hydrophobic benefit agents. Other suitable benefit agents are described in U.S. patent application Ser. No. 13/157,665. The benefit phase may also comprise a dried zinc pyrithione.

Non-limiting examples of glycerides suitable for use as hydrophobic skin benefit agents herein can include castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, and combinations thereof.

Non-limiting examples of alkyl esters suitable for use as hydrophobic skin benefit agents herein can include isopropyl esters of fatty acids and long chain esters of long chain (i.e. C10-C24) fatty acids, e.g., cetyl ricinoleate, non-limiting examples of which can include isopropyl palmitate, isopropyl myristate, cetyl riconoleate, and stearyl riconoleate. Other examples can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use as hydrophobic skin benefit agents herein can include oleyl myristate, oleyl stearate, oleyl oleate, and combinations thereof.

Non-limiting examples of polyglycerin fatty acid esters suitable for use as hydrophobic skin benefit agents herein can include decaglyceryl distearate, decaglyceryl diisostearate, decaglyceryl monomyriate, decaglyceryl monolaurate, hexaglyceryl monooleate, and combinations thereof.

Non-limiting examples of lanolin and lanolin derivatives suitable for use as hydrophobic skin benefit agents herein can include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, and combinations thereof.

Non-limiting examples of silicone oils suitable for use as hydrophobic skin benefit agents herein can include dimethicone copolyol, dimethylpolysiloxane, diethylpolysiloxane, mixed C1-C30 alkyl polysiloxanes, phenyl dimethicone, dimethiconol, and combinations thereof. Nonlimiting examples of silicone oils useful herein are described in U.S. Pat. No. 5,011,681. Still other suitable hydrophobic skin benefit agents can include milk triglycerides (e.g., hydroxylated milk glyceride) and polyol fatty acid polyesters.

III. Procedures

A. Drying Techniques Used for Preparing Dried Zinc Pyrithione

Spray Drying

Zinc pyrithione can be obtained as a slurry of a 49% active suspension of Fine Particle Size (FPS) Zinc Omadine®, which is stabilized by surface-adsorbed polynaphthalene sulfonate. The zinc pyrithione particles have a mean diameter of about 0.75 microns as determined by light scattering. A slurry was spray dried using a Büchi Mini Spray Dryer B290 with an inlet temperature of 200° C. and an outlet temperature of 100° C. The slurry flow rate was controlled by adjusting the peristaltic pump control to 35% of a maximum pump speed. The compressed air flow rate for a feed dispersion was set to approximately 600 L/hr. The spray-dried zinc pyrithione aggregate particles are observed to have particle size of about 10 microns to about 100 microns by light microscopy with an average diameter of about 60 microns, while being comprised of distinct primary particle subunits, which are the original FPS particles. The particles are spherical. Void space between the primary particles can increase an apparent surface area of the aggregate such that the particle can have properties such as a dissolution rate governed by the specific interface of the primary particles, about $9 \times 10^5$ cm$^2$/cm$^3$. Advantageously, the particle is disintegrable, or frangible, under reasonable application of force, fracturing under applied pressure to a microscope cover slip.

Tray Drying

Zinc pyrithione can be obtained as a slurry of a 49% active suspension of Fine Particle Size (FPS) Zinc Omadine®, which is stabilized by surface-adsorbed polynaphthalene sulfonate. The FPS zinc pyrithione particles have a mean diameter of about 0.75 microns as determined by light scattering. The slurry was placed in an aluminum foil boat, which was subsequently placed into a drying oven (temperature=45° C.). Once thoroughly dry, the material was removed from the foil and mechanically broken into small particles. The fractions were sieved using U.S. Standard Sieves to yield particle-size fractions based on the sieve mesh sizes indicated.

B. Pig Skin Residual Efficacy Test

To prepare a placebo, perform a one wash/rinse performance protocol. In particular, generate an overnight bacterial culture of *E. coli* (strain 10536, 8879, or 11259) by inoculating 50 mL of TSB with one colony obtained from a Tryptic Soy Agar (TSA) streak plate. Grow the culture for 17-18 hr, 37° C., 200 rpm in a dry shaker.

To determine efficacy of a bar soap, perform bar soap ex vivo performance tests on pigskins. First, obtain, clean, refrigerate, and irradiate (25-40 kGy) the pigskins. Store the irradiated pigskins at −20° C. until testing. To test bar soap compositions, thaw 10×10 cm pigskins to room temperature for 1 hour, and cut the pigskins into 5×10 cm sections using a sterile scalpel.

Using a gloved hand, wash the pigskins as follows: Rinse a 5×10 cm pigskin for 15 seconds, with tap water at 33-36° C. with a flow rate of 4 to 4.2 L/min. Wet the bar soap composition in the running water for 5 seconds, lay the bar composition flat on the pigskin surface, then immediately rub the bar soap composition gently across the entire pigskin surface for 15 seconds using back and forth motions and light hand pressure similar to that during conventional hand washing. Then, generate lather by continuously rubbing the pigskin for 45 seconds with the hand (e.g. absent the bar soap composition). Rinse the pigskin with tap water for 15 seconds by holding the tissue at a 45 degree angle and allowing the water to impinge on the top surface and cascade downwards across the entire surface. Lightly pat the pigskin dry with a sterile tissue, and allow the pigskin to dry for 5-10 minutes in still room air under low light conditions.

Cut the pigskin into 2×2.5 cm slices and inoculate each slice with 106-107 cfus by using 10 µL of a 1:20 dilution of Tryptic Soy Broth (TSB) obtained from an overnight culture as described above. Allow the bacteria to dry on the slice of the pigskin surface for 20 minutes, then place the slice of the pigskin into a humidified chamber (60% RH, 33° C.), and incubate the slices for 0 hours, 2 hours, or 5 hours. After incubation, place the slice into a jar containing 50 mL of ice cold neutralization buffer of Modified Leethen Broth with 1.5% Tween-80 and 1% Lecithin (MBL-T), and vigorously shake the buffer with the slice therein for 1 minute to elute bacteria. As necessary, dilute the suspension in MBL-T and place the suspension onto Tryptic Soy Agar (TSA) plates to obtain cell counts. Incubate the plates for 24 hours, at 33° C., and 60% Relative Humidity. Then, count the TSA plates (e.g. the cfus thereof) to calculate the cfu/mL and generate a growth curve using GraphPad Prism v4.1. Perform the test described above once to calculate the cfu/mL and to generate the growth curve. (Note: The test described above can also be performed multiple times and the data for each repetition can be averaged).

C. Cup Scrub Procedure for Measuring Deposition

As noted herein, the Cup Scrub Procedure can be used to assist in determining how much zinc-containing and/or pyrithione material is deposited onto a pig skin. First, wet a target substrate surface under running water (flow=4.5 L/min, temp=35-38° C.) for approximately 15 seconds. Next, apply a dose of 1 mL of body wash (via disposable syringe) to the target substrate surface. Proceed to generate lather on the target substrate by rubbing the applied body wash by hand for approximately 15 seconds. Following the 15-second lathering process, the lather is allowed to sit undisturbed on the pig skin for an additional 15 seconds. At the end of the 15-second wait (30 seconds after the start of the lathering process), rinse the pig skin for approximately 10 seconds, allowing the running water to contact the target substrate surface and cascade down (toward the distal surface). Following the rinse, use a paper towel to pat the surface dry.

The next part of the procedure involves a 2-cm diameter glass cylinder containing a bead of silicone caulking on a skin contact edge which will be pressed firmly against a pig skin surface to prevent leakage of an extraction fluid. One mL of the extraction solvent can be pipetted into the glass cylinder. To determine how much zinc pyrithione is deposited, for example, the extraction solvent can be 80:20 0.05 M EDTA: EtOH. While using a transfer pipette or glass rod, an entire area within the glass cylinder can be scrubbed for about 30 seconds using moderate pressure. The solution can be removed and pipetted into a labeled glass sample vial. The Cup Scrub Procedure can be repeated using fresh extraction solution, which will be pooled with the initial extraction in the labeled vial.

After each use, the glass cylinder and rod can be cleaned. The cleaning can be done, for example, by immersing each cylinder and rod in dilute Dawn® solution and scrubbed with a finger or soft bristle brush. The cylinders and rods can then be immersed in IPA. Finally, cylinders and rods can be wiped dry with a Kimwipe or other lint free tissue to remove any visible residue. Scrub solutions can be changed at an end of each day or when any visible layer of residue can be found in the bottom thereof. Further, samples can be stored at 4° C. (±3° C.) until the samples can be submitted for HPLC analysis. HPLC analysis is then used to determine the amount of deposition. The free pyrithione in solution is then derivatized with 2-2'-Dithiopyridine, and subsequently analyzed via HPLC utilizing UV detection. The results are reported as µg of zinc pyrithione per mL of solution.

D. Cantilever Compliance Test

Cantilever compliance is a measure of an article's ability to conform in shape under an applied force. Cantilever compliance is determined by creating a cantilever with the article and measuring the deflection under applied stress. Preferably, the length and width of the article are determined and the article is arranged as a cantilever such that ¾ of the length protrude past the supporting structure. A weight is affixed to the cantilever end of the article using binder clips, the total applied weight should represent typical forces exerted on an article used for cleansing and can range from 0.05-0.75 kg. The deflection of the cantilever in the vertical direction is measured and divided by ¾ of the length of the article and multiplied by 100 to obtain the value for cantilever compliance. Cantilever compliance=100*(D/(0.75*L))

The method can be repeated to determine the cantilever compliance of the article in terms of width of the article. Cantilever compliance=100*(D/(0.75*W))

In this fashion the cantilever compliance of an article can be determined in both the machine and cross machine directions, where cross machine is defined as perpendicular to the direction in which articles move through the assembly process.

E. Compliance Test

To measure the compliance of a personal care article or composition, use a Texture Analyzer TA-XT2i (Texture Technologies Corp, NY, USA) equipped with at least a 5 kg load cell and a 0.75 inch ball probe at ambient conditions, with the probe zero point at an article top surface using 0.5 gram-force to register a probe height, and a 2 gram-force to commence data collection for both force and distance. Measure a compressive force (kg) at a compression rate of 1 mm/sec over a depth of 5 mm, ensuring that the personal care article or composition form a flat surface over contact area with the ball probe, near the center of the article or composition. Repeat measurements as needed (e.g., at least 3 times) to obtain a representative average value. To determine the compliance of the article or composition divide the maximum observed force (kg) by the maximum compression depth (5 mm). When using a 5 kg load cell some samples may exceed capacity, in this case the maximum compression depth will be less than the set depth of 5 mm, specified in the procedure.

F. Consumption Rate Test

To measure the Consumption Rate of a personal care article or composition, use a rotary tumbler (Lortone, Inc., Seattle, Wash., USA model 33B or equivalent) with 4 in. diameter by 4 in. deep cylindrical rubber housing having 825 cc internal volume. The housing revolves on the tumbler at 43 rpm. Obtain a supply of tap water at about 7.5 grains water hardness and conductivity between 100 to not more than 400 microSemens per centimeter ($\mu$S/cm) and heat in a reservoir beaker to 45° C. Maintain the water supply at the target temperature within 1 degree for the test duration. Add 200.0 gm water from the reservoir to the housing. Weigh an article or composition to obtain the initial weight, and add the article or composition to the housing. Seal the housing with its accompanying watertight lid and place the sealed housing onto the rotary tumbler for exactly 3 minutes. Remove the housing, remove the housing lid, and retrieve the article or composition. Stir the remaining water in the housing for a few seconds and measure its conductivity and temperature using a Mettler Toledo Seven multimeter with InLab 740 probe or equivalent. Dry the article or composition surface by pressing, not rubbing, using paper towels with light hand pressure for about 30 seconds, until it is dry to the touch and transfers no more visible water to a dry paper towel using the same pressure at any point on its surface or edges. If the article or composition transfers partially dissolved or dissolving components in addition to liquid water, for example if the composition is a conventional bar soap it may transfer paste-like material, the transferred components are to be removed and the article or composition is considered dry when visible transfer is no longer evident. Weigh the article or composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of enhancing deposition of zinc pyrithione to skin, comprising: applying a cleansing composition to at least a portion of the skin of an individual and then applying a composition comprising zinc pyrithione to the same portion of skin of the individual.

2. The method of claim 1, wherein the cleansing composition and the zinc pyrithione composition occupy separate areas on a bar soap.

3. The method of claim 2, wherein the bar soap has two sides and the cleansing composition is located on one side and the zinc pyrithione composition is located on the other.

4. The method of claim 2, wherein the bar soap is wrapped in a substrate to form a personal care article.

5. The method of claim 4, wherein the personal care article is conformable.

6. The method of claim 2, wherein the bar soap is compliant.

7. The method of claim 1, wherein the skin is rinsed prior to application of the zinc pyrithione composition.

8. The method of claim 1, wherein the personal cleansing composition and the zinc containing composition are part of a multi-zone personal care article.

9. The method of claim 8, wherein the multi-zone personal care article comprises a first water penetrable substrate.

10. The method of claim 9, wherein the first water penetrable substrate comprises a first zone and a second zone.

11. The method of claim 10, wherein the zinc containing composition is located in the first zone and the cleansing composition is located in the second zone.

12. The method of claim 8, wherein the multi-zone personal care article is conformable.

13. A method of enhancing deposition of zinc pyrithione to skin, comprising: formulating a personal care composition comprising zinc pyrithione with about 15% or less, by weight of the composition, of wax.

14. The method of claim 13, wherein the personal care composition comprises about 12% or less, by weight of the composition, of wax.

15. The method of claim 13, wherein the personal care composition is substantially free of surfactant.

16. The method of claim 13, wherein the personal care composition is free of surfactant.

17. The method of claim 13, wherein the personal care composition is a benefit phase.

18. The method of claim 17, wherein the benefit phase comprises a benefit agent comprising soybean oil.

* * * * *